United States Patent
Anderton et al.

(10) Patent No.: US 10,436,937 B2
(45) Date of Patent: Oct. 8, 2019

(54) DETECTION DEVICE

(71) Applicant: QINETIQ LIMITED, Farnborough, Hampshire (GB)

(72) Inventors: Rupert Nicholas Anderton, Worcester (GB); Richard George Humphreys, Malvern (GB)

(73) Assignee: QINETIQ LIMITED (GB)

(*) Notice: Subject to any disclaimer, the term of this patent is extended or adjusted under 35 U.S.C. 154(b) by 0 days.

(21) Appl. No.: 16/081,695

(22) PCT Filed: Mar. 2, 2017

(86) PCT No.: PCT/EP2017/054956
§ 371 (c)(1),
(2) Date: Aug. 31, 2018

(87) PCT Pub. No.: WO2017/149094
PCT Pub. Date: Sep. 8, 2017

(65) Prior Publication Data
US 2019/0094411 A1 Mar. 28, 2019

(30) Foreign Application Priority Data
Mar. 3, 2016 (GB) .................................. 1603716.0

(51) Int. Cl.
*G01V 8/18* (2006.01)
*G01V 8/00* (2006.01)
*G02B 26/10* (2006.01)

(52) U.S. Cl.
CPC ............... *G01V 8/18* (2013.01); *G01V 8/005* (2013.01); *G02B 26/108* (2013.01)

(58) Field of Classification Search
CPC .. G02B 26/101; G02B 26/105; G02B 26/126; G02B 26/108; G01V 8/005; G01V 8/18
See application file for complete search history.

(56) References Cited

U.S. PATENT DOCUMENTS 7,271,899 B2    9/2007  Anderton et al.
2005/0274890 A1* 12/2005 Anderton ............... G01V 8/005
                                                250/334

FOREIGN PATENT DOCUMENTS

| GB | 1 562 599 | 3/1980 |
| GB | 2 256 937 | 12/1992 |
| GB | 2448077 | 10/2008 |

(Continued)

*Primary Examiner* — David P Porta
*Assistant Examiner* — Fani Boosalis
(74) *Attorney, Agent, or Firm* — McDonnell Boehnen Hulbert & Berghoff LLP (57) ABSTRACT

The present invention discloses a detection device for discriminating between different materials, and a method for doing so. The device comprises an optical system having at least one optical focussing element and a receiving element. The receiving element is sensitive to electromagnetic radiation, typically in the millimeter wave band, and the optical system being arranged to focus incident energy from a scene onto the receiving element. The optical system comprises a prism element having a first surface and a second surface, the first surface being opposite the second surface. At least a portion of the first surface is positioned at an angle θ to the second surface. The angle θ varies between a minimum at a first position on the first surface and a maximum at a second position on the first surface.

17 Claims, 3 Drawing Sheets

(56) References Cited

FOREIGN PATENT DOCUMENTS

| JP | S63121009 | 5/1988 |
| JP | H07 239405 | 9/1995 |
| JP | H1144750 | 2/1999 |
| WO | WO 2012/040749 | 4/2012 |

* cited by examiner

DETECTION DEVICE

FIELD OF THE INVENTION

The present invention relates to a detection device, in particular a detection device for discriminating between different materials, comprising an optical system having at least one optical focussing element, an optical scanning element and a receiving element, wherein the receiving element is sensitive to electromagnetic radiation, preferentially radiation in the millimeter wave band, and where the optical system arranged to focus incident energy from a scene onto the receiving element.

BACKGROUND OF THE INVENTION

Millimeter wave radiation systems are commonly used in security settings to identify high risk objects and materials by scanning a scene and using radiation reflected by or emitted by objects within the scene to determine the identity of various objects. Typically such systems produce an image of the radiometric brightness temperature of the scene at frequencies between around 30 GHz up to around 300 GHz. Many such systems tend to be passive and operate using a scanning mechanism, as described below.

One such system, as disclosed in U.S. Pat. No. 7,271,899 scans a receive beam of radiation from two or more points on a scene (typically a subject such as a person). A comparison is made between the radiometric brightness temperature of the points measured to determine any differences, which are subsequently used to detect the presence of an anomaly that may pose a security threat, such as a weapon or explosive device. In the case where two measurement points on a target are used, A beam of radiation is scanned sequentially from the two points using an optical system that passes the radiation through a two sector prism (see FIG. 15 of '899) after forming it into a parallel beam, where each sector produces a receive-beam in a given direction. The parallel beam may be formed by collection optics such as an afocal telescope, alternatively the prism may be located between the scene and the collection optics where the radiation is substantially parallel. This prism comprises a shallow cone sector structure and a shallow inverted cone sector structure, and is rotated about a central axis such that the beam passes through the prism off-axis close to the edge of the prism whilst it rotates. In order to scan a scene the two (or more) points on the target may be moved in an approximate square wave pattern, up, across, down, across, up, across and so on to cover the entire scene, which may typically be performed manually by an operator commanding a pan and tilt head. US'899 also discloses a rotating prism (see FIG. 7), which produces a circular scan of a beam on the target.

Although highly effective a manual scan is time-consuming, since the operator must scan the scene whilst interpreting the sensor response at each position scanned. For example, an entire torso must be scanned and any resulting alarm indications examined. This reduces the efficiency of the overall process, which may cause issues in high traffic areas requiring such scans.

One alternative is to use a system generating multiple beams in a vertical line, so that several beams at once pass over the scene. This means that an operator merely has to scan across the scene horizontally, rather than also vertically. Such a linear beam system may be produced by using a prism with several shallow cone sectors and shallow inverted cone sectors each of different opening angles, so that when the prism is rotated several beams are generated. So the prism itself is divided into zones, each zone a different cone sector, such that each zone is responsible for the formation of an individual beam. Although this arrangement offers several advantages over a two-beam system, it does have the disadvantage that there is an increasing proportion of dead time (time where measurements are not taking place, which occurs when the beam is cut by the transition between two zones) in the scan, as the number of zones increases. This reduces integration time and hence signal to noise ratio. This is not proportional to the number of beams formed. For instance, in a known implementation the reduction in signal to noise ratio for four beams is, for example, a factor of 1.95 compared to a two beam, approach or single beam switched between two different directions. For six beams the reduction is 2.83, and more than six beams becomes impractical due to the requirements placed on the size of the prism. In addition the response of the receiving element is highly dependent on the vertical position of the target area in the vertical line consisting of the multiple beams. For example, a target centred on a beam will produce a different response to one centred on the mid-point between two adjacent beams. This can create issues in determining the most appropriate detection algorithm to use to ensure reliability, and so may decrease performance in terms of hit rate and false alarm rate. Using improved sampling by increasing the number of beams formed that cover a given vertical angle may aid in reducing algorithm-related issues but the increase in the number of beams causes the integration time and signal to noise ratio to worsen yet further. There is therefore a need to be able to find a solution that overcomes the issues in sampling without detriment to the signal quality.

SUMMARY OF THE INVENTION

In a first aspect, the present invention aims to address these issues by providing a detection device for discriminating between different materials, comprising an optical system having at least one optical focussing element, an optical scanning element and a receiving element, wherein the receiving element is sensitive to electromagnetic radiation, the optical system being arranged to focus incident energy from a scene onto the receiving element via the optical scanning element, wherein the optical scanning element has a first surface having a region with a continuously variable angle with respect to a second surface of the optical scanning element, wherein the continuously variable angle acts to provide a continuously variable scan of the scene.

Advantageously, the optical scanning element comprises a prism element having a first surface and a second surface, the first surface being opposite the second surface and at least a portion of the first surface being positioned at an angle θ to the second surface, and wherein the angle θ varies between a minimum at a first position on the first surface and a maximum at a second position on the first surface. The prism may be a transmissive prism, that is arranged to refract the energy passing therethrough.

Alternatively, the optical scanning element may be arranged to have a reflective surface on the region having the continuously variable angle, and is arranged to reflect electromagnetic energy from the scene onto the receiving element. In such embodiments, the optical scanning element may comprise of a metal, or metal coated disk having a reflective surface as described.

The following description is based upon the optical element being comprised of a transmissive prism, but the normally skilled person will appreciate where the various variants may be applied to an embodiment having a reflective optical element.

Preferably, the angle θ varies continuously across the first surface between the first position and the second position on the first surface. In some embodiments therefore, the prism, instead of having a small number of zones with each zone forming a separate beam, effectively has an infinite number of zones and so has a smoothly varying surface.

In some embodiments the outer edge of this first surface at the circumference of the prism forms a spiral or helix coaxial to the axis of rotation of the prism. Some embodiments may have an inner hub to the prism which is flat and that contains the axle rotating the prism. The inner edge of the first surface may also form a spiral or helix at the outer edge of this hub, the spiral or helix being in an opposite direction to that spiral or helix at the outside circumference of the whole prism. This hub is advantageously made small enough so that the entirety of the parallel beam passing through the prism misses the hub.

By using a prism having at least a portion of the first surface having a varying angle with respect to the second surface it is possible to create a continuous linear scan using a single beam, thus removing the issues created by dead time and minimising signal to noise ratio effects. Signal quality therefore remains high when compared with using many individual beams to perform a scan.

Preferably, the angle θ varies continuously across the first surface between the first position and the second position on the first surface.

Preferably, the first surface comprises an interface between the second position on the first surface and the first position on the first surface where the angle θ changes sharply, thus acting as a flyback at the end of the vertical scan. Thus, this provides a scan from a first position on the target to a second position during movement of the prism from first to the second position. Alternatively the angle θ may increase from a minimum to a maximum value and then back again to the minimum value over one rotation of the prism. This provides a scan from the first position, to the second position and back to the first during a full rotation of the prism. This has a benefit in that no discontinuous interface is formed in the first surface, but this arrangement leads to a steeper pitch to the spiral formed between the edge of the first surface and the edge of the second surface and thus increases optical aberration. The aberration increases with increased curvature across that part of the prism that is, at any given instant, involved in refracting incoming radiation.

Most preferably, the prism is cylindrical in outline, such that the first surface and the second surface have a circular planform (i.e. when viewed along the axis of the prism), and form the circular ends of the cylinder.

Preferably, the first surface is described using a Cartesian co-ordinate system with z both parallel to the prism axis of rotation and, in some embodiments, normal to the flat prism surface and where $r^2=x^2+y^2$ the angle θ is described by:

$$\tan\theta = \frac{dz}{dr}$$

Preferably, the prism has a central axis perpendicular to the first surface and the second surface planform, and wherein the prism is mounted so as to rotate around the central axis.

Preferably, the receiver is sensitive to millimeter wave radiation, such as radiation in the band between 30 GHz and 300 GHz, although it will be appreciated by the normally skilled person that it will have utility outside of this range. The receiver may be arranged to have a bandwidth of sensitivity within this frequency range, typically between 1 GHz and 35 GHz, Bands of interest may be chosen according to criteria such as availability of receivers, likelihood of environmental interference, target emissivity or reflectivity characteristics etc.

Preferably the rotation of the prism forms a swept beam of millimeter wave radiation in a continuous linear scan.

Preferably the device is arranged to receive millimeter wave radiation, that is fed through the prism, where the received radiation is emitted by, or reflected from the target which has emanated from the surrounding environment, and does not comprise of radiation transmitted by the device through the prism. Thus, such devices may be passive devices, in that they rely on naturally occurring millimeter wave radiation, or they may be passive devices wherein the background radiation levels are augmented by one or more non-coherent millimeter wave noise sources, such as heaters, white noise generators, or the like. Such passive systems simplify the system design, and also provide reassurance that the systems are safe to use from the point of view of targets being subject to radiation.

At some point on the rotation of the prism, the first surface may be, at one or more points of angular position on the active region of the prism, parallel to the second surface, or may otherwise be angled so as to retro-reflect energy from the receive element. This may, e.g. in embodiments where the prism is mounted with a face of the prism normal to the axis of a subsequent receive antenna, result in spurious radiation emitted by the receiver antenna bouncing back from one or both of the prism faces into the antenna, and hence producing a false signal at that particular angular position of rotation. A similar problem, that of retro-reflections from one or both faces back into the receive element, can occur even when the axis of the prism is offset, in situations where the refraction of radiation through the prism results in energy being reflected from both surfaces, or the angle of the surface facing the receive element is such that retro-reflection can occur.

Some embodiments of the invention may have a prism that is arranged in use to have a prism that reflects energy emanating from the receive element from at least one of the first and second surface away from the receive element at all angular positions of the prism.

Accordingly, some embodiments may be arranged to have, at a localised region on the prism, a deviation in both the first and second surfaces from their curvature at other regions, whilst maintaining a continuously variable angle between the two. At this localised region, the same deviation is applied to both the first and second surfaces. The curvature deviation should be made sufficient to ensure reflections from the receive element do not go back towards the receive element or antenna (used synonymously herein). The localised region will include the angular point on the prism where energy emanating from the receive element is reflected back to the receive element from the first and second surfaces of the prism. Where the prism is mounted axially parallel with the receive element, this angular point will be where both the first and second surfaces are parallel to each other. Note that one of the surfaces, typically the surface that is furthest from the receiving element, may have, for all but this localised region, a curvature of zero, it being planar, with the plane normal to the optical axis of the receiving element.

Where the prism is not mounted axially parallel with the receive element, the region will include the point where refraction of the energy within the prism results in the retro-reflection of energy from one or both surfaces travelling back to the receive element.

The deviation in curvature of the first and second surfaces at the localised region on the prism is preferably chosen to be sufficient so that any energy emitting from the receiving element is reflected back to a region away from the receiving element.

The curvature deviation applied may comprise of a first fixed positive angular deviation, followed by a second fixed negative angular deviation to bring the first and second surfaces away, and then back to the curvature of the rest of the prism. Alternatively, the curvature deviation may comprise in the localised region a more gradual, continuously varying deviation from the curvature of the rest of the prism.

In a second aspect, the present invention provides a method of detecting objects present in a scene by means of receiving electromagnetic radiation from the scene, comprising the steps of:
  receiving a beam of electromagnetic radiation from the scene using an optical system;
  forming, from the received radiation, a beam of electromagnetic radiation internal to the sensor system;
  scanning the internal beam, and hence also the external beam, using a moving element having a surface wherein at least a portion of the surface positioned at an angle $\theta$ to a notional plane running through the element, wherein the angle $\theta$ varies between a minimum at a first position on the surface and a maximum at a second position on the surface, and wherein the scanned internal beam produces, for at least a portion of the element's movement, a continuous scan of the external beam.

Advantageously, the moving element is a prism, and the surface constitutes a first surface, the prism also having a second surface, the first surface being opposite the second surface with at least a portion of the first surface being positioned at an angle $\theta$ to the second surface, wherein the angle $\theta$ varies between a minimum at a first position on the first surface and a maximum at a second position on the first surface, Advantageously, the beam of electromagnetic radiation is a collimated beam. The optical system may be arranged to produce the collimated beam, using, for example, an afocal telescope arrangement. Use of a collimated beam can help to keep the size of the optics down, and also helps to reduce vignetting.

Preferably, the prism is arranged to rotate about an axis, wherein said rotation acts to provide a scan of the beam direction.

In some embodiments the scan produced by the prism is substantially linear.

In some embodiments the scan produced by the prism may occur substantially in a first dimension, and a second dimension may be scanned by effecting movement of the whole optical system. Preferably, the first direction is horizontal and the second direction is vertical.

Preferably, the angle $\theta$ varies continuously across the first surface between the first position and the second position on the first surface.

Preferably, the first surface comprises an interface between the first position on the first surface and the second position on the first surface where the angle $\theta$ changes sharply. This interface provides a "flyback" function to the beam, moving the beam from a finishing point of its continuous scan back to a starting point. Continued rotation of the prism causes this scan-flyback process to cycle repeatedly.

Most preferably, the prism is cylindrical, such that the first surface and the second surface have a circular planform and form the circular ends of the cylinder.

Preferably, the first surface is described using a Cartesian co-ordinate system with z both parallel to the prism axis of rotation and normal to the flat prism surface and where $r^2=x^2+y^2$, and the angle $\theta$ is described by:

$$\tan\theta = \frac{dz}{dr}$$

Preferably, the prism has a central axis perpendicular to the first surface and the second surface planform, and wherein the prism is mounted so as to rotate around the central axis.

Preferably, the rotation of the prism creates the continuous linear scan over at least some part of a full rotation period.

In some embodiments, signals generated within the receiver due to the incoming EM radiation are processed, using techniques such as those disclosed in U.S. Pat. No. 7,271,899, the contents as they relate to the detection of objects and discriminating between different target materials, are incorporated herein by reference. The signals received may, for example, be processed to detect a change in signal strength throughout the scan, which may be indicative of the presence of a material of interest. Advantageously, some embodiments may be arranged to process the received signals without forming an image using the signals, where an image in this context comprises of a 2D array of pixels that provide, for a given scene, a resolution at least that of the Johnson criteria for recognition. Further processing methods are described with respect to specific embodiments below, but are applicable more widely to other embodiments also.

A further aspect of the invention provides a detection device for discriminating between different materials, comprising an optical system having at least one optical focussing element, an optical scanning element and a receiving element, wherein the receiving element is sensitive to electromagnetic radiation, the optical system being arranged to focus incident energy from a scene onto the receiving element via the optical scanning element, wherein the optical scanning element comprises a prism element having a first surface and a second surface, the first surface being opposite the second surface and at least a portion of the first surface being positioned at an angle $\theta$ to the second surface, and wherein the angle $\theta$ varies between a minimum at a first position on the first surface and a maximum at a second position on the first surface.

A yet further aspect of the invention provides a method of detecting objects present in a scene by means of receiving electromagnetic radiation from the scene, comprising:
  receiving a beam of electromagnetic radiation from the scene using an optical system;
  forming, from the received radiation, a beam of electromagnetic radiation internal to the sensor system;
  scanning the internal beam, and hence also the external beam, using a moving prism element having a first surface and a second surface, the first surface being opposite the second surface and at least a portion of the first surface being positioned at an angle $\theta$ to the second surface, wherein the angle $\theta$ varies between a minimum at a first position on the first surface and a maximum at a second position on the first surface, and wherein the scanned internal beam produces, for at least a portion of the prism's movement, a continuous scan of the external beam.

Previously discussed variants and features of embodiments of the invention are equally applicable, where appropriate, to these further aspects of the invention.

DESCRIPTION OF THE DRAWINGS

The present invention will now be described in detail, by way of example only, and with reference to the accompanying drawings, in which.

DESCRIPTION OF THE INVENTION

In order to overcome the issues associated with increased sampling, signal to noise ratio, integration time and algorithm efficiency, the present invention proposes the use of a continuous scan created using a novel prism arrangement, as described in more detail below. A detection device for discriminating between different materials comprises an optical system having at least one optical focussing element and a receiving element. The receiving element is sensitive to millimeter-wave radiation, making it suitable for use in various applications where it is necessary to determine the presence of materials or to distinguish between materials. The optical system is arranged to focus incident energy from a scene onto the receiving element, and comprises a prism element in addition to a focussing element. The prism element has a first surface and a second surface, the first surface being opposite the second surface and positioned at an angle θ to the second surface. The angle θ varies between a minimum at a first position on the first surface and a maximum at a second position on the first surface. When the prism revolves the continuous change in the surface of the prism creates a beam of radiation that continuously varies its scan direction, as opposed to a number of discrete beams formed in an aligned manner.

Figure 1:
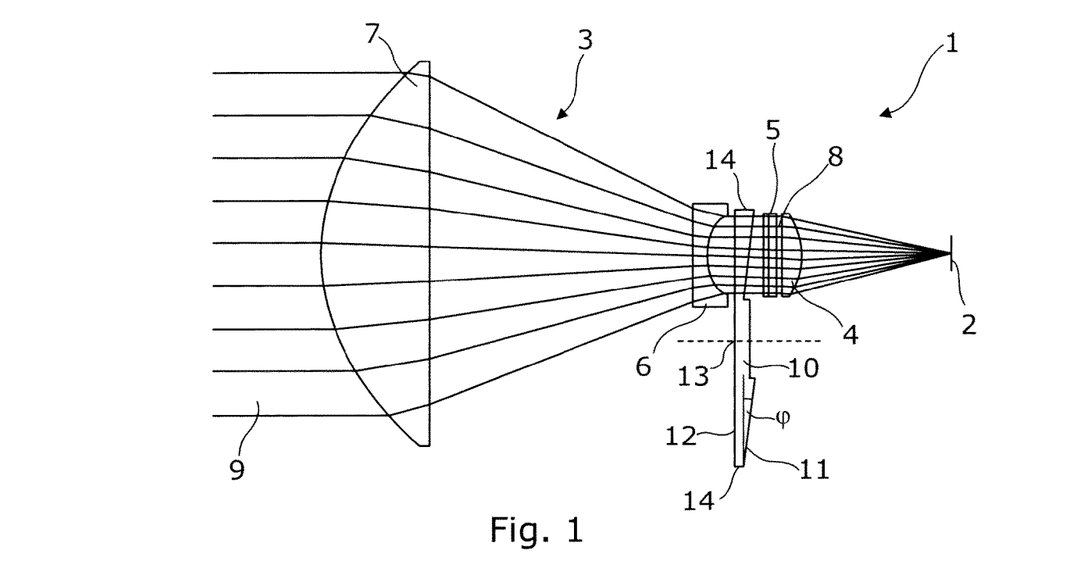
FIG. 1 is a schematic cross-sectional view of an optical system for use in a detection device in accordance with an embodiment of the present invention.

FIG. 1 is a schematic cross-sectional view of an optical system for use in a detection device in accordance with an embodiment of the present invention. The optical system 1 comprises a receiving element 2, in optical alignment with an afocal telescope arrangement 3, plus a scanning prism 10, and a quarter wave plate 5 to act as an isolator for reflections from the prism and a small convex lens 4 to focus radiation onto the receiving element. Other embodiments may forego the quarter wave plate if such reflections are not a problem. The afocal telescope arrangement 3 comprises a first convex lens element 7, and a concave lens 6. Each lens element is formed from a high density polythene material having a refractive index of approximately 1.5 in the millimeter wave band 30 GHz to 300 GHz. Radiation from the scene, that is the object or subject requiring analysis to discriminate between materials, is collected as a large diameter collimated beam by the afocal telescope 3, passing first through the large convex lens 7 and then the small concave lens 6, thus forming a smaller diameter collimated beam 8 upon exiting lens 6. The collimated beam passes through the prism 10, and then through the quarter-wave plate 5, converting from circular to linear polarisation. This collimated beam is then focussed onto the receive element 2 by the small convex lens 4. The preferred receive element is a millimeter-wave horn with a radiation pattern matched to the diameter of the small convex lens 4.

The quarter wave plate 5 reduces the magnitude of any spurious emitted radiation due to the receive element/antenna 2, such as its own noise temperature or local oscillator leakage, that reflects from the prism 10 and is received back at the receive element 2 as a time varying signal. For example, if vertical polarisation is emitted by the receive element 2, it will be converted to for example right hand circular polarisation by the quarter wave plate 5 before reflecting off the prism 10 as left-hand circular polarisation. The quarter-wave plate 5 will then convert this left-hand circular polarisation to horizontal polarisation which will be rejected by the vertically polarised receive element 2. If the quarter wave plate is omitted, the system will receive linear polarisation rather than circular polarisation, but that makes no significant difference to the signature received in the typical wavebands of interest, however the system will be more prone to error due to receiving its own emission reflected off the prism. However, some embodiments may do without the quarter-wave plate 5. Other embodiments may seek to provide further reduction of the effects of spurious emitted radiation, by using the technique discussed in relation to FIG. 5, which may be used instead of, or as well as, the quarter wave plate 5.

The prism element 10 is positioned between the concave lens element 6 and the quarter-wave plate 5 such that radiation exiting the concave lens element 6 is incident on the prism 10 before reaching the quarter-wave plate 5. The prism 10 has a first surface 11 and a second surface 12, the first surface 11 being opposite the second surface 12. The prism 10 is cylindrical in outline, such that the first surface 11 and the second surface 12 are planform circular and form the ends of the cylinder. The second surface 12 is plane. The prism 10 is provided with a central axis 13 that defines a z axis and perpendicular to the second surface 12, and is mounted so as to rotate around the central axis 13. The prism 10 is positioned with the central axis 13 laying below the collimated beam 8, such that only a portion of the prism 10 is positioned within the collimated beam 8 at any point during its rotation. Effectively only a portion laying between the central axis 13 and the circumference 14 of the circular prism 10 is within the collimated beam 8 at any one moment in time. Those portions of the prism involved in refracting desired radiation may be collectively termed the active part of the prism.

As indicated above, the first surface 11 is positioned opposite the second surface 12. At least a portion of the first surface 11 is positioned at an angle θ to the second surface 12, and wherein the angle θ varies between a minimum at a first position 16 on the first surface 11 and a maximum at a second position 15 on the first surface 11. This is shown in more detail in FIGS. 2 and 3.

Figure 2:
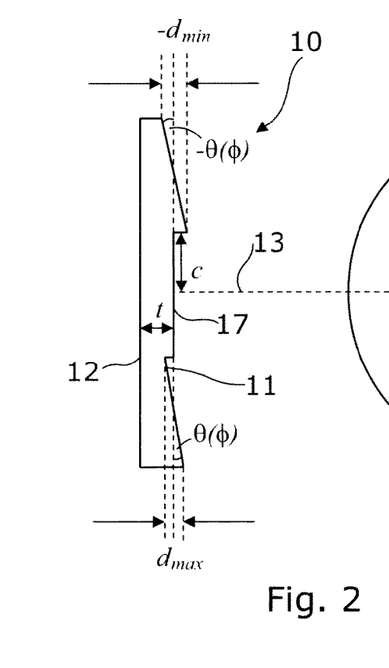
FIG. 2 is a schematic side view of the surface of a prism for use in an optical system employed in embodiments of the present invention.

FIG. 2 is a schematic side view of the surface of a prism for use in an optical system employed in embodiments of the present invention. The first surface 11 of the prism 10 is provided with a central flat hub portion 17 having a radius c, where the first surface 11 and the second surface 12 are positioned a constant thickness t apart. Between the central portion 17 and the circumference 14 of the prism 10 the angle θ(φ) the first surface 11 makes with the second surface 12 varies with rotation angle φ: φ=arctan(y/x). In the cross-section shown an upper portion of the first surface 11 is inclined at an angle $-\theta(\phi)$ to the second surface 12, and a lower portion of the first surface 11 is inclined at an angle $+\theta(\phi)$ to the second surface 12. The distance parallel to the z axis between the point closest to the central portion 17 and the point closest to the circumference 14 in the upper portion at the first position 16 is $-d_{min}$, and the distance parallel to the z axis between the point closest to the central portion 17 and the circumference 14 in the lower portion at the second position 15 is $+d_{max}$. The flat central portion 17 is positioned at $-d_{min}/2$ or $+d_{max}/2$.

Figure 3:
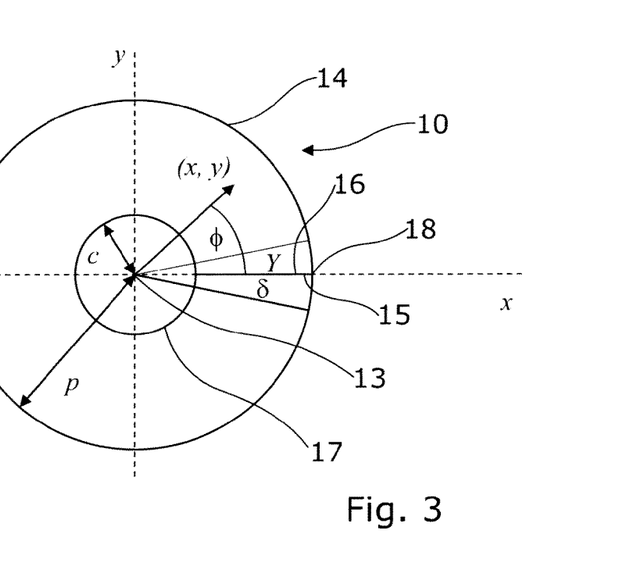
FIG. 3 is a schematic representation of the surface of a prism shown in FIG. 2.

FIG. 3 is a schematic representation of the surface of a prism shown in FIG. 2. The first surface 11 is described using a Cartesian co-ordinate system, where any point on the first surface 11 may be described as a position in terms of (x, y). It is not possible to have a continuously varying surface across the whole of the prism, unless $\theta$ increases smoothly both from an minimum value to a maximum value and then back again which is undesirable due to increased curvature, and hence increased aberrations, as described above, therefore an interface 18 where the angle $\theta$ changes sharply exists, between the first position 16 and the second position 15. It is also desirable to have regions at either end of the scan i.e. on either side of the interface 18 where the angle $\theta$ between the first surface 11 and the second surface 12 does not change, essentially forming two 'flat ends' to the scan. This avoids the signal to noise ratio at the edges of the scan from being worse than in the rest of the scan. The flat ends occur where $0 \leq \phi \leq \gamma$, and when $2\pi - \delta \leq \phi \leq 2\pi$. The radius of the entire prism 10 may be described by $\rho$, and the equations defining the surface of the prism 10 in radians are:

$$r = \sqrt{x^2 + y^2}$$

$$\alpha = \arctan\left(\frac{d_{min}}{\rho - c}\right)$$

$$\beta = \arctan\left(\frac{d_{max}}{\rho - c}\right)$$

Solving these equations for $\phi$ gives:

$$\theta = \alpha: \phi \leq \gamma$$

$$\theta = \alpha + (\phi - \gamma)\left(\frac{\beta - \alpha}{2\pi - \delta - \gamma}\right): \gamma < \phi < 2\pi - \delta$$

$$\theta = \beta: \phi \geq 2\pi - \delta$$

$$\phi = \arctan(y/x)$$

To ensure that all of the values of $\phi$ between 0 and $2\pi$ are obtained:

$\phi = \arctan|y/x|: x > 0, y > 0$ $\phi = \pi - \arctan|y/x|: x < 0, y > 0$ $\phi = \pi + \arctan|y/x|: x < 0, y < 0$ $\phi = 2\pi - \arctan|y/x|: x > 0, y < 0$ The surface sag (z axis coordinate) is given by $$sag = t - \left[r - \left(\frac{c + \rho}{2}\right)\right]\tan\theta$$

OSLO (Optics Software for Layout and Optimisation, available from Lambda Research Corporation, 25 Porter Road, Littleton, Mass. 01460, USA, optimised for version 6.0.1) is a software tool used to design lenses, although it will be appreciated by those of ordinary skill in the art that other suitable software packages are available. Using such a program, user defined surface macros, which return a function Uds_f=0, can be set up to describe the surface:

$$\text{Uds\_f} = z - sag = z - t + \left[r - \left(\frac{c + \rho}{2}\right)\right]\tan\theta: r > c$$

$$\text{Uds\_f} = z - t: r \leq c$$

OSLO also requires the partial derivatives with respect to x, y and z of Uds_f as follows, providing r>c:

$$\text{Uds\_f} = z - t + \left[r - \left(\frac{c + \rho}{2}\right)\right]\tan\theta$$

$$\frac{d}{dx}\text{Uds\_f} = \left[r - \left(\frac{c + \rho}{2}\right)\right]\frac{d}{dx}\tan\theta + \tan\theta\frac{dr}{dx}$$

$$= \left[r - \left(\frac{c + \rho}{2}\right)\right]\sec^2\theta\frac{d\theta}{dx} + \tan\theta\frac{d}{dx}\sqrt{x^2 + y^2}$$

Now $$\frac{d\theta}{dx} = 0: \phi \leq \gamma$$

$$\frac{d\theta}{dx} = \left(\frac{\beta - \alpha}{2\pi - \delta - \gamma}\right)\frac{d\phi}{dx}: \gamma < \phi < 2\pi - \delta$$

$$\frac{d\theta}{dx} = 0: \phi \geq 2\pi - \delta$$

So $$\frac{d}{dx}\text{Uds\_f} = \frac{x}{r}\tan\theta: \phi \leq \gamma$$

$$\frac{d}{dx}\text{Uds\_f} = \left[r - \left(\frac{c + \rho}{2}\right)\right]\left(\frac{\beta - \alpha}{2\pi - \delta - \gamma}\right)(1 + \tan^2\theta)\frac{d\phi}{dx} + \frac{x}{r}\tan\theta: \gamma < \phi < 2\pi - \delta$$

$$\frac{d}{dx}\text{Uds\_f} = \frac{x}{r}\tan\theta: \phi \geq 2\pi - \delta$$

Also $$x = r\cos\phi \quad y = r\sin\phi$$

$$1 = \frac{dr}{dx}\cos\phi - r\sin\phi\frac{d\phi}{dx}$$

$$y\frac{d\phi}{dx} = \frac{x^2}{r^2} - 1$$

$$\frac{d\phi}{dx} = \frac{x^2 - y^2}{yr^2}$$

$$= \frac{-y}{r^2}$$

Similarly:

$$\frac{d\phi}{dy} = \frac{x}{r^2}$$

So given $r > c$, $$\frac{d}{dx}\text{Uds\_f} = \frac{x}{r}\tan\theta: \phi \leq \gamma$$

$$\frac{d}{dx}\text{Uds\_f} =$$

$$\frac{x}{r}\tan\theta - \left[r - \left(\frac{c + \rho}{2}\right)\right]\left(\frac{\beta - \alpha}{2\pi - \delta - \gamma}\right)\frac{y}{r^2}(1 + \tan^2\theta): \gamma < \phi < 2\pi - \delta$$

$$\frac{d}{dx}\text{Uds\_f} = \frac{x}{r}\tan\theta: \phi \geq 2\pi - \delta$$

Similarly:

$$\frac{d}{dy}\text{Uds\_f} = \frac{y}{r}\tan\theta: \phi \leq \gamma$$

$$\frac{d}{dy}\text{Uds\_f} =$$

$$\frac{y}{r}\tan\theta + \left[r - \left(\frac{c+\rho}{2}\right)\right]\left(\frac{\beta-\alpha}{2\pi-\delta-\gamma}\right)\frac{y}{r^2}(1+\tan^2\theta): \gamma < \phi < 2\pi - \delta$$

$$\frac{d}{dy}\text{Uds\_f} = \frac{y}{r}\tan\theta: \phi \geq 2\pi - \delta$$

If $r <= c$ $$\frac{d}{dx}\text{Uds\_f} = \frac{d}{dy}\text{Uds\_f} = 0$$

Also for all r and φ, $$\frac{d}{dz}\text{Uds\_f} = 1$$

These equations can then be used to define the first surface 11 of the prism 10.

Figure 4:
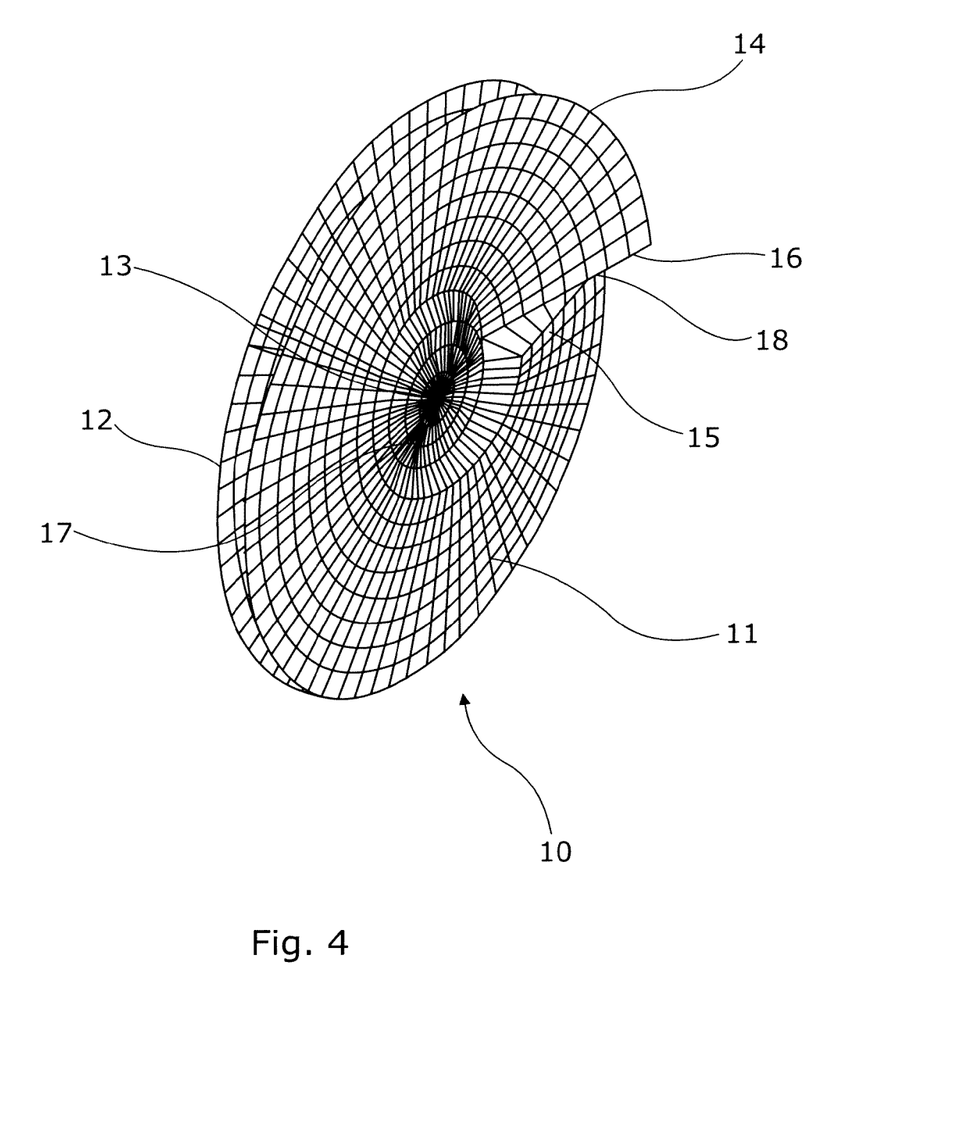
FIG. 4 is a schematic perspective view of the prism shown in FIGS. 2 and 3.

FIG. 4 is a schematic perspective view of the prism shown in FIGS. 2 and 3. This illustrates that the angle θ between the first surface 11 and the second surface 12 varies continuously form a minimum to a maximum value during one revolution of the prism 10, apart from at each 'flat end'. The interface 18 where the angle changes sharply only intersects the 32 mm diameter radiation beam transiting the 100 mm diameter prism for 16% of the rotation of the prism if the beam is offset by 33 mm from the prism axis, thus the prism is relatively efficient with only 16% dead time.

In this embodiment the maximum thickness of the prism 10 is 12.044 and the minimum thickness 2 mm when formed from a polythene material having a refractive index of approximately 1.5 in the millimeter-wave band to enable it to be used with existing optical systems. The diameter of the prism is 100 mm, $d_{max} = -d_{min} = 10.044$ mm, c=15 mm, t=7.022 mm and γ=δ=54.17 degrees. The prism is used with an afocal telescope of aperture 150 mm forming a collimated beam through the prism of diameter 32 mm, and the effect of the prism is to scan the instantaneous vertical field of view of the afocal telescope through approximately ±1.9 degrees. This is equivalent to collecting data over 6 beamwidths of the afocal telescope when operating at the preferred frequency of 183 GHz.

In order to integrate the data obtained to reduce noise and therefore increase the signal to noise ratio a rolling average of the data obtained is taken over a single rotation of the prism 10, although a matched filter may be used as an alternative. This results in a reduction in signal to noise ratio of a factor of approximately 1.51, compared with that of the standard two-spot system described in U.S. Pat. No. 7,271,899. However this compares very favourably with the signal-to-noise reduction by a factor of 1.95 for a prism made of 4 discrete zones scanning the afocal telescope over only 4 beamwidths rather than 6 beamwidths. The optical performance of the prism 10 in the preferred embodiment is diffraction limited throughout the field of view, with Strehl intensity of at least 85% predicted by OSLO throughout the field of view. A small sideways deflection of the collimated beam 9 is generated, but is equivalent to −0.1° in object space and varies little with scan position, so has little overall effect on the data obtained.

In use, the prism is employed in a method of detecting objects present in a scene by means of receiving millimeter wave radiation from the scene. Levels of threat (the presence of various materials) are determined from the radiometric temperature of the scan, with variations in temperature within the continuous linear scan being compared with each other to determine the threat level. The processing of data received from the scene is discussed in more detail below. A collimated beam 9 of millimeter wave radiation from the target is collected by the afocal telescope. The scene is then scanned in a first direction by moving the whole optical system. The internal collimated beam 8 is scanned using the prism element 10 described above, and this in turn causes the collimated beam 9 to form a continuous linear scan in a second direction, the second direction being perpendicular to the first direction. So, if the first direction of the collimated beam 9 is horizontal, scanning across the scene, the second direction in which the beam is spread is vertical. As an alternative, if appropriate and desired, the first direction may be vertical and the second direction may be horizontal. Only a single scan movement of the whole optical system is therefore required.

Note that if the prism angle θ cannot be considered to be small, and a scan linear with time is required, then if Δ is the angular deviation of mm-wave radiation caused by the prism, strictly the requirement is $$\Delta = \Delta_{min} + \phi\left(\frac{\Delta_{max} - \Delta_{min}}{2\pi}\right)$$

Where $\Delta_{min}$ and $\Delta_{max}$ are the end of scan angular radiation deviations towards the axis and away from the axis respectively.

Given that the front face 12 of the prism is flat (as per the typical implementation), then the prism angle θ may be found using:

$$\Delta = \arcsin(n \sin\theta) - \theta$$

where n is the refractive index of the material the prism is made from. α and β may be found similarly from $\Delta_{min}$ and $\Delta_{max}$.

Various algorithms may be used to process the data obtained using the optical system 1 described above. Data is output in a continuous stream from the receiving element at time intervals T from the commencement of the prism scan until its termination. The scan is used to determine threat points in relation to the radiometric temperature of the scan, that is, a low temperature point represents a high threat, in other words, a material requiring investigation is present, and a high temperature point represents a low threat. This may be used, for example, when scanning a subject for a weapon or explosive material at an airport or other secure location.

The simplest way to process the data is to average the input data stream $y_i$ into overlapping segments w units wide spaced w/2 apart, where w is the collimated beam 9 width (full-width half maximum FWHM).

Each point at which a difference in materials resulting in a threat level will be calculated has a signal given by:

$$V_j = \frac{\sum_{i=i\,min_j}^{i\,max_j} y_i}{i\,max_j - i\,min_j + 1}$$

Where $V_j$ is a signal at a threat point j, $$c(j) = \frac{j(q+1)}{n+1}$$

is the index of the centre time point at the centre of threat point j, q is the number of time steps per scan, and $$r = \frac{w-1}{2},$$

$i$ $\min_j=\text{int}(c(j)-r+0.5), i$ $\max_j=\text{int}(c(j)+r+0.5)$.

Rounding causes the threat points to be spaced in a non-uniform manner, but the worst case error should correspond to <T/2. For a six-spot scan with eleven points, and T=1.56 ms, a beam width corresponds to ~9 points, therefore the centre of the average will only be in error by 1/18 of a beam width. A Gaussian filter of the form $$g(x, w) = \frac{\sqrt{\ln(16)}}{w\sqrt{\pi}} e^{\frac{-4 \ln(2)x^2}{w^2}}$$

may be used, where w is the full width at half maximum of the Gaussian. It is sufficient to use points with x ranging from −w to w, where the units used are time, time step number, or number of beam widths, as desired. Other algorithms, such as those based upon averaging between temperature points in a scan, determining a mean temperature or deviation from a mean temperature may be used as alternatives for determining a threat level from the data received from the receiving element.

In the above embodiment a single variation of angle θ between a minimum and a maximum is used. However, it may be desirable to vary the angle θ between more than one minimum and maximum point, for example, where two such variations are included in a single rotation of the prism 10, however this tends to increase optical aberration. It may also be desirable that rather than only a portion of the first surface 11 being positioned at an angle θ to the second surface 12 that the flat central portion 17 is removed, and the whole of the first surface 11 is positioned at an angle θ with respect to the second surface 12 where the angle θ varies continuously between a minimum at a first position on the first surface 11 and a maximum at a second position on the first surface.

Figure 5:
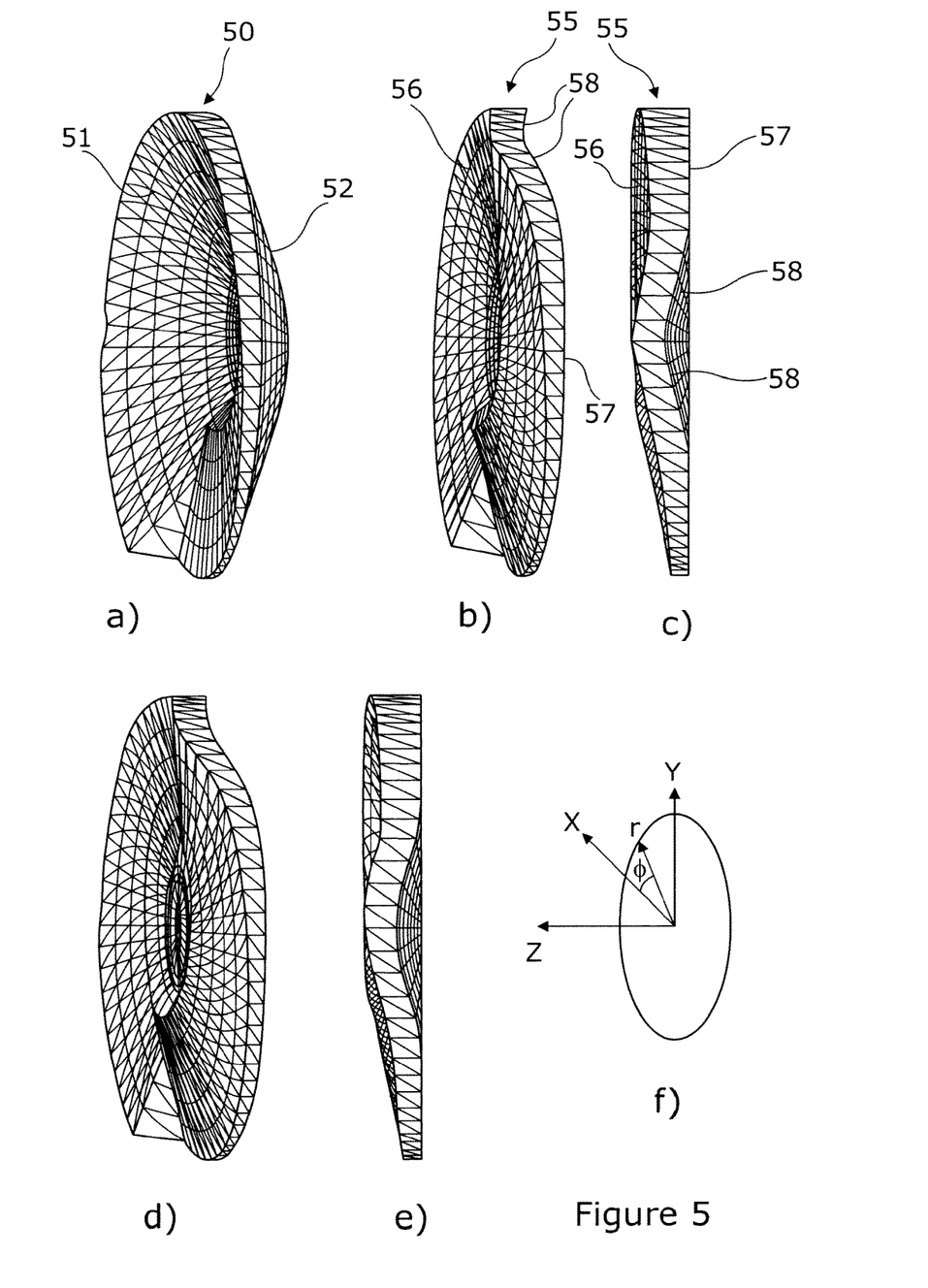
FIG. 5 shows schematic representations of three alternative prism arrangements.

FIG. 5 shows three examples of prisms that are designed to prevent retro-reflections of energy emanating from the receive element, and which may be used in embodiments of the present invention. The prisms have an active portion in a radial band around their centre, not including the centre itself, which is used to scan energy from a scene onto the receive element as shown in FIG. 1, in broadly similar fashion to the prism of FIG. 2. All these prisms of FIG. 5 however are arranged to prevent retro-reflection of energy back towards the receive element. In each case the radial gradient of the prism is constant, i.e. dz/dr is constant for any one value of rotation angle ϕ, where sag is in the axial z direction and $r^2=x^2+y^2$ (where the co-ordinate system is shown in FIG. 5f).

FIG. 5a shows a first prism 50 that has a first surface 51 and a second surface 52 that have (as with the other prisms shown herein) a continuously varying angular relationship to each other as the prism is rotated about its axis (the z axis). Thus, energy that passes through a part of the prism in the z direction is refracted according to known principles by an amount dependent upon the angular difference between the first and second surfaces. The angular relationship of the first and second surfaces is chosen so as to provide a linear scan of the energy emanating from a remote target onto the receive element. It will be seen that, in contrast to the previously shown embodiments, the prism has a generally conic form, having a slope in the z axis as it moves along a radius line, in both the first and second surfaces. The slope is chosen so that retro-reflection from the receiver element does not occur at any position during a full rotation of the prism.

FIGS. 5b and 5c show two views of a prism 55 having first 56 and second 57 surfaces that again have a continuously varying angular relationship between each other, and so act to provide a linear scan of energy passing through an active portion the prism. The prism 55 has a linear deviation 58 in the z axis around the point in Φ where the first and second surfaces are parallel to each other. It will be seen that energy impinging upon a surface 56 of the prism and arriving parallel to the axis thereof will be reflected back dependent upon the angle of the surface 56, and (via refraction through the material of the prism) of the angle of the surface 57. Where the deviation 58 (as compared to the prism of FIG. 2) occurs, the angular relationship between the two surfaces is the same as in the other parts of the prism, hence scanning of the beam occurs as before but the faces are no longer parallel to the axis of the prism, and so there will be no retro-reflection back to the receiver element.

FIGS. 5d and 5e show a further embodiment of a prism designed to avoid retro-reflections. Again, the prism has two surfaces, that have a constantly varying angular relationship to each other, seen as the prism rotates as before. It is broadly similar to the embodiment of FIGS. 5b and 5c, but differs in that instead of having a linear deviation in the z axis at a region where the two surfaces become parallel to each other, it has a gradually changing deviation. This avoids the sharp transitions of the embodiment of FIG. 5b, which might reduce refracted image quality, A circumferential profile of the form (1+cos ϕ) is used in the deviation region, although it will be appreciated that other curves could also be used, as would be understood by a normally skilled person.

Describing this embodiment more precisely, then assuming the prism interface (as defined in relation to ref. 18 in FIG. 3) is at ϕ=0 and the deviation region starts and finishes at ϕ=180°±μ, then a suitable equation for change in sag—i.e. the z coordinate of the surface (compared to the standard prism of FIG. 2, for both surfaces)—is $$\Delta z = G(r-c) \frac{\left[1 + \cos\left(\frac{180°\{\phi - 180°\}}{\mu}\right)\right]^n}{2^n} : r > c, |\phi - 180°| < \mu$$

$$\Delta z = 0: \text{elsewhere}$$

where an inner radius of the active region of the prism is c, G is the maximum desired radial gradient of the deformation (e.g. to keep the prism inside a desired size envelope) i.e. G=dz/dr at ϕ=180°, and n>0.5 is chosen for optimum performance. The value of n and μ are advantageously chosen to minimise the peak retro-reflected energy over a complete revolution of the prism, and may be done by running simulations with suitable optical design software. Smaller values of p reduce the angular extent over φ of the deviation, and larger values of n increase the gradient of the deviation over φ near the centre of the deviation at the expense of the gradient near the edges of the deviation, i.e. sharpen the peak of the deviation. A value of n greater than 0.5 is beneficial in that it gives a smooth transition between the deviated and non-deviated parts of the surface.

The materials from which the prism and lenses may be made will depend upon the exact optical qualities required, and may be selected according to their loss, and refractive index, to provide desired optical characteristics. Although polythene has been used in the embodiments described above, other materials, such as PTFE, Rexolite or other plastics, as would be understood by those of ordinary skill in the art.

These and other embodiments of the present invention will be apparent from the appended claims.

The invention claimed is:

1. A detection device for discriminating between different materials, comprising an optical system having at least one optical focussing element, an optical scanning element and a receiving element, wherein the receiving element is sensitive to millimeter-wave electromagnetic radiation, the optical system being arranged to focus incident energy from a scene onto the receiving element via the optical scanning element, wherein the optical scanning element is a transmissive prism, and has a first surface having a region with a continuously variable angle with respect to a second surface of the optical scanning element, wherein the continuously variable angle acts to provide a continuously variable scan of the scene, and wherein the prism is arranged to rotate around a central axis to provide a linear scan of the beam direction.

2. Detection device of claim 1 wherein the optical scanning element comprises a prism element having a first surface and a second surface, the first surface being opposite the second surface and at least a portion of the first surface being positioned at an angle θ to the second surface, and wherein the angle θ varies between a minimum at a first position on the first surface and a maximum at a second position on the first surface.

3. Detection device of claim 2, wherein the angle θ varies continuously across the first surface between the first position and the second position on the first surface.

4. Detection device of claim 2, wherein the first surface comprises an interface between the first position on the first surface and the second position on the first surface where the angle θ changes sharply.

5. Detection device of claim 2, wherein the prism is cylindrical in outline, such that the first surface and the second surface are planform circular and form the circular ends of the cylinder.

6. Detection device of claim 5, wherein the first surface is described using a Cartesian co-ordinate system with z parallel to the prism rotation axis and where the angle θ is described by:

$$\tan\theta = \frac{dz}{dr}, \text{ where } r^2 = x^2 + y^2$$

7. Detection device of claim 5, wherein the prism has a central axis perpendicular to the first surface and the second surface, and wherein the prism is mounted so as to rotate around the central axis.

8. Detection device of claim 2, wherein the rotation of the prism generates a beam of electromagnetic radiation in a continuous linear scan.

9. Detection device of claim 2 wherein the prism is arranged in use to reflect energy emanating from the receive element from at least one of the first and second surface away from the receive element at all angular positions of the prism.

10. Detection device of claim 9 wherein the prism has a localised region thereon, a deviation in both the first and second surfaces from their curvature at other regions, whilst maintaining a continuously variable angle between the two.

11. A detection device as claimed in claim 1 wherein the device is arranged to detect radiation produced by the target, or radiation reflected from the target emanating from the surrounding environment.

12. A detection device as claimed in claim 11 wherein the amount of radiation within a detection bandwidth of the device in the environment is augmented using a noise source.

13. Method of detecting objects present in a scene by means of receiving millimeter-wave electromagnetic radiation from the scene, comprising:
  receiving a beam of electromagnetic radiation from the scene using an optical system;
  forming, from the received radiation, a beam of electromagnetic radiation internal to the sensor system;
  scanning the internal beam, and hence also the external beam, using a moving, rotating element comprising a transmissive prism having a surface wherein at least a portion of the surface is positioned at an angle θ to a notional plane running through the element, wherein the angle θ varies between a minimum at a first position on the surface and a maximum at a second position on the surface, and wherein the scanned internal beam produces, for at least a portion of the element's movement, a continuous scan of the external beam, and wherein the prism is arranged to rotate around a central axis to provide a linear scan of the beam direction.

14. A method as claimed in claim 13 wherein the moving element is a transmissive prism, and the surface constitutes a first surface, the prism also having a second surface, the first surface being opposite the second surface and at least a portion of the first surface being positioned at an angle θ to the second surface, wherein the angle θ varies between a minimum at a first position on the first surface and a maximum at a second position on the first surface.

15. Method of claim 14, wherein the scan produced by the prism occurs substantially in a first dimension, and further wherein a second dimension is scanned by effecting movement of the whole optical system.

16. Method of claim 13 wherein the beam formed from the received radiation is a collimated beam.

17. Method of claim 13 wherein the method is implemented on a device comprising an optical system having at least one optical focussing element, an optical scanning element and a receiving element, wherein the receiving element is sensitive to millimeter-wave electromagnetic radiation, the optical system being arranged to focus incident energy from a scene onto the receiving element via the optical scanning element, wherein the optical scanning element is a transmissive prism, and has a first surface having a region with a continuously variable angle with respect to a second surface of the optical scanning element, wherein the continuously variable angle acts to provide a continuously variable scan of the scene, and wherein the prism is arranged to rotate around a central axis to provide a linear scan of the beam direction.

* * * * *